(12) United States Patent
Tesini

(10) Patent No.: US 11,033,463 B2
(45) Date of Patent: Jun. 15, 2021

(54) PACIFIER FITTING SYSTEM AND METHOD

(71) Applicant: David A. Tesini, Hopkinton, MA (US)

(72) Inventor: David A. Tesini, Hopkinton, MA (US)

( * ) Notice: Subject to any disclaimer, the term of this patent is extended or adjusted under 35 U.S.C. 154(b) by 51 days.

(21) Appl. No.: 16/166,775

(22) Filed: Oct. 22, 2018

(65) Prior Publication Data

US 2019/0117520 A1 Apr. 25, 2019

Related U.S. Application Data

(60) Provisional application No. 62/575,040, filed on Oct. 20, 2017.

(51) Int. Cl.
*A61J 17/00* (2006.01)
*A61J 11/00* (2006.01)

(52) U.S. Cl.
CPC ............ *A61J 17/113* (2020.05); *A61J 11/007* (2013.01); *A61J 17/001* (2015.05); *A61B 2503/04* (2013.01); *A61J 11/005* (2013.01)

(58) Field of Classification Search
CPC ....... A61C 7/002; A61J 17/001; A61J 17/008; A61J 11/005; A61J 11/007; A61J 17/113; A61B 2503/04; G06K 9/00281
See application file for complete search history.

(56) References Cited

U.S. PATENT DOCUMENTS

| | | | | |
|---|---|---|---|---|
| 5,659,625 A * | 8/1997 | Marquardt | ......... | G06K 9/00268 345/634 |
| 5,867,588 A * | 2/1999 | Marquardt | ......... | G06K 9/00281 382/118 |
| 6,080,186 A * | 6/2000 | Pedersen | ................ | A61J 17/107 606/234 |
| 9,855,194 B1 * | 1/2018 | Walter, Jr. | ............ | A61J 11/0095 |
| 2007/0238063 A1 * | 10/2007 | Tesini | .................... | A61J 17/001 433/7 |
| 2010/0063543 A1 * | 3/2010 | Moses | .................... | A61J 17/107 606/236 |
| 2012/0053631 A1 * | 3/2012 | Tesini | .................... | A61J 17/008 606/234 |
| 2012/0257162 A1 * | 10/2012 | Encaoua | .............. | G02C 13/005 351/204 |
| 2014/0014118 A1 * | 1/2014 | Cuevas | .................. | A61J 17/107 128/861 |
| 2014/0270406 A1 * | 9/2014 | George | .............. | G06K 9/00268 382/118 |
| 2015/0262422 A1 * | 9/2015 | Znamenskiy | ...... | G06K 9/00201 345/420 |
| 2015/0374303 A1 * | 12/2015 | Gelbman | ............... | A61B 5/746 600/476 |

(Continued)

OTHER PUBLICATIONS

Bishara et al., "Arch width changes from 6 weeks to 45 years of age", Am J Orthod Dentofacial Orthop., vol. 111, No. 4 (1997), pp. 401-409. (Year: 1997).*

(Continued)

*Primary Examiner* — Nay A Maung
*Assistant Examiner* — Jose M Torres
(74) *Attorney, Agent, or Firm* — Brian M. Dingman; Dingman IP Law, PC

(57) ABSTRACT

A system and method for fitting pacifiers and other implements to a particular child. One or more images of the child are used to determine anthropometric data that can be used to properly size a pacifier bulb and properly fit other implements.

12 Claims, 4 Drawing Sheets

(56) References Cited

U.S. PATENT DOCUMENTS

2017/0068846 A1* 3/2017 Linguraru .......... G06K 9/00288

OTHER PUBLICATIONS

Levrini et al., "Different geometric patterns of pacifiers compared on the basis of finite element analysis", European Journal of Paediatric Dentistry, vol. 8, No. 4 (2007), pp. 173-178. (Year: 2007).*

Cordeiro et al., "Study of the correlation between the linear measurements of the skull and face and palatal wide and length measures", CoDAS vol. 27, No. 5m Sao Paulo, Sep./Oct. 2015, pp. 472-477 (Year: 2015).*

* cited by examiner

PACIFIER FITTING SYSTEM AND METHOD

CROSS-REFERENCE TO RELATED APPLICATION

This application claims priority of Provisional Patent Application Ser. No. 62/575,040 filed on Oct. 20, 2017.

BACKGROUND

This application relates to fitting pacifiers and other implements to a particular child.

Pacifier sizing is typically based solely on the age of the child. However, children of the same age are not the same height or weight, and do not have the same facial characteristics such as palate, lips, nose and chin. Infant facial structure varies by age, gender, weight, genetic characteristics and ethnicity and other factors. The size of the palate increases as much in the first two years of life as it does from age 3 to 45. The bulb of the pacifier needs to fit to the palate. Using the proper bulb size is important in proper function and preventing orthodontic and jaw alignment problems later.

The pacifier shield is equally important, as it is often not designed or sized properly for the child's face. Companies focus on comfort and aesthetic design rather than important fit and function issues such as lip support and free mandibular movement. Shield designs may also be customized to the child's face depending on their lips, nose and jaw growth. The shield prevents aspiration of the device during sucking and is structured to comply with Consumer Product Safety Commission requirements. Lateral facial profile characteristics determine the fit of the shield against the face and the resulting encumbrance and force impact against the mandible. Certain lateral facial characteristics and mandibular posture may also be related to sudden infant death syndrome (SIDS). Free movement of the mandible downward and forward is well known to provide airway enhancement. Shield patents have recognized the importance of free mandibular movement during nutritive and non-nutritive sucking. Pressure by the shield against the mandible inhibits desired forward posturing.

SUMMARY

Featured in this disclosure are systems and methods for properly fitting pacifiers and other objects that are designed to be held or used in a child's mouth, such other objects including but not limited to objects related to soothing and/or feeding a child, which would include objects such as drinking spouts, bottle nipples, a lid for or the lip of a drinking cup, and other dental and orthodontic appliances. The systems and methods can also be used to properly fit a shield of a pacifier. Fitting can include (but is not limited to) one or more of the size, shape, orientation, hardness and distortion of the object being fitted.

The fit of pacifiers and shields are important as they affect acceptance, comfort, soothing, breathing and the growth and development of the face of a growing child.

The palate is a hidden structure to the lens of a camera recording a facial image. Unlike other systems which collect measurement data on images and then directly apply that data for fitting of clothes, glasses, hats, etc., the subject software application is configured to calculate the size of the palate from anthropometric correlations of other visual facial structures, points and landmarks and quantitatively relate that to palatal size. Anthropometry is the biological science of human body measurement. The fitting can be based on calculations derived from one or more images of the infant/child. The fitting in one non-limiting example is based at least in part on the use of facial anthropometric data. The data can be obtained by any useful means. In one non-limiting example the data are based on one or more images of the particular child. The images can include a front view and/or a side (profile) view. One or more identified anthropometric points and resulting measurements or estimates based on the images are then obtained and used to accomplish the fit. The sizing can then be used in the fabrication of devices such as a bulb and/or a shield. The fabrication can be by 3D printing. This might allow sizing changes as frequently as the user would like in the same manner that parents buy bigger clothes as the baby grows.

DETAILED DESCRIPTION

Figure 1:
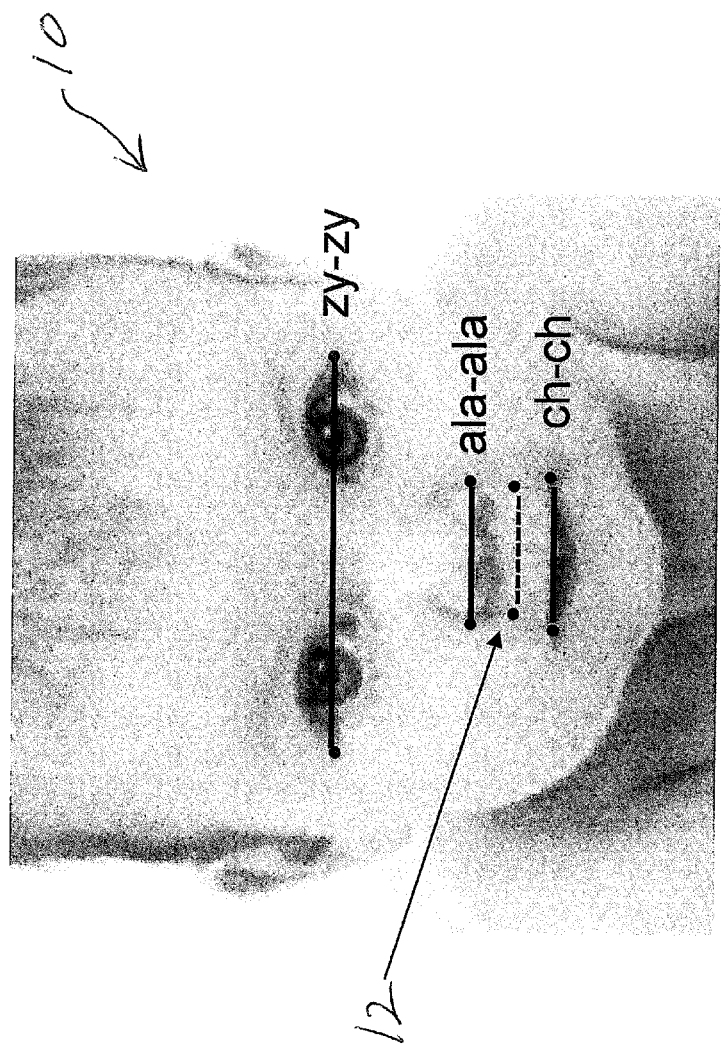
FIG. 1 is a front view of an infant with certain identified anthropometric points.

In one non-limiting example the types of facial anthropometric data that are used include one or more of the following:

The inner inter-canthal distance
The outer inter-canthal distance
The inter-pupillary distance
The oral inter-commissural distance
The bizygomatic width
The palatal width
The nasal width
The ratio of nasal/mouth width
The lip length
The facial height
The mandibular index These measurements of distance, length, width, height, etc. are then used to populate an algorithm of correlations and/or facial indices. These correlations have been calculated from research data obtained from peer reviewed scientific literature. As the available scientific literature is updated then this new published data can be used as it relates to palatal width and mandibular size.

Infant physical characteristics are quantifiable. These include length, weight, head circumference, body mass, and tooth eruption. Alone they provide no means to predict palatal size. Likewise, image generated anthropometric facial data is quantifiable, but standing alone, provides no means to predict palatal size.

The subject system and method allows the use of infant physical data and infant anthropometric facial data to be populated into various equations with correlations that provide weighted significance. These equations, related correlations and facial indices can be generated specific to cohort characteristics such as nationality, prematurity, genetic syndromes, metabolic diseases etc., which may alter the correlations between physical and facial characteristics and palatal size.

In a like manner, the system and method provides a fitting method for pacifier shields. The pacifier shield is a required portion of all oral soothing devices for infants and the size and design are in part determined by standards of consumer protection. The system and method provides analysis which can include mandibular size, mandibular position and mandibular relationships to other facial structures. In particular, the shapes of pacifier shield vary greatly from one company to another. Most recently U.S. Pat. No. 9,308,152 (the disclosure of which is incorporated herein by reference for all purposes) provides a unique advantage for infant growth with a design that removes the shield impingement on the mandible. This design further demands that knowledge of lateral (profile) characteristics can be identified, quantified, and integrated into an algorithm of correlations including the relationship to mandibular position and mandibular size.

Following is a non-limiting example of how the system and method can be used to calculate biometric sizing of a pacifier bulb. Following are some of the anthropometric terms and abbreviations used herein.
Nasion (Na): The mid-point on the soft tissue contour of the base of the nasal root at the level of the frontonasal suture
Otobasion inferius (OBI): The point of attachment of the ear lobe to the cheek, which determines the lower border of the ear insertion
Alare (abbreviated as either ala or al): The most lateral point on each alar contour
Cheilion (Ch): The point located at each labial commissure
Zygion (Zy): Most lateral point of the zygomatic arch
Gnathion (Gn): The most anterior-inferior mid-point of the chin
A=Age (months)
W=Weight (kg or lbs.)
MW=Width of Mouth (chelion-chelion (ch-ch) in mm)
FW=Width of Face (Zygoma-zygoma (Zy-Zy) in mm)
PW=Width of palate (as is known in the field, the width of the palate can be extrapolated from the following reference, the disclosure of which is incorporated herein by reference: Bishara et al. Am J Orthod Dentofac Orthop 1997; 111:401-9).

FIG. 1 includes an image 10 of an infant with the zy-zy, ala-al, and ch-ch points and widths indicated thereon, as well as the calculated palatal width 12.

Any one or more of such types of anthropometric data can be used at least in part to determine the best fit. Other factors that can be considered in determining best fit include age, gender, weight, height, ethnicity and facial type.

Figure 2:
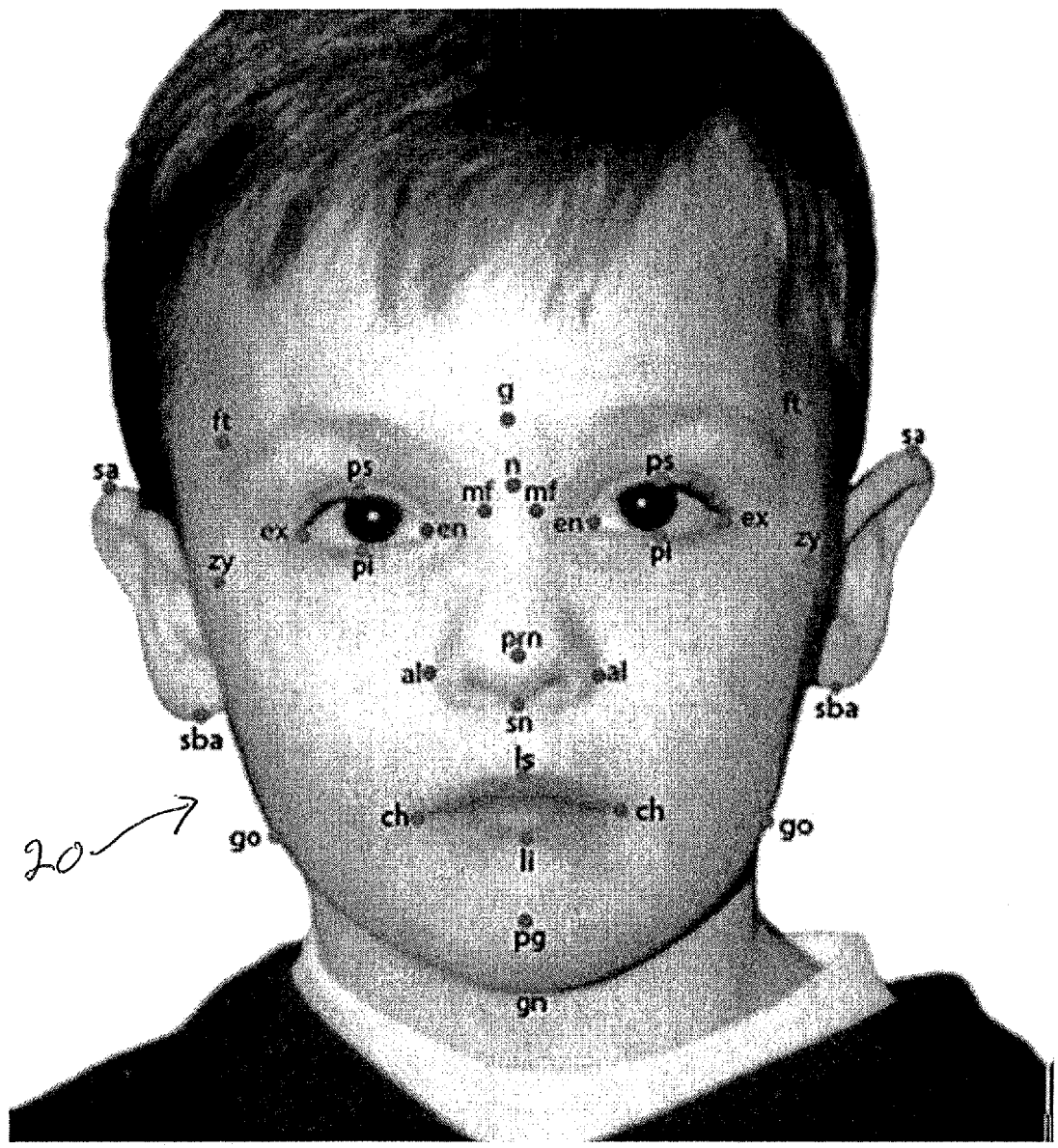
FIG. 2 is a front view of an infant with certain identified anthropometric points.
Figure 3:
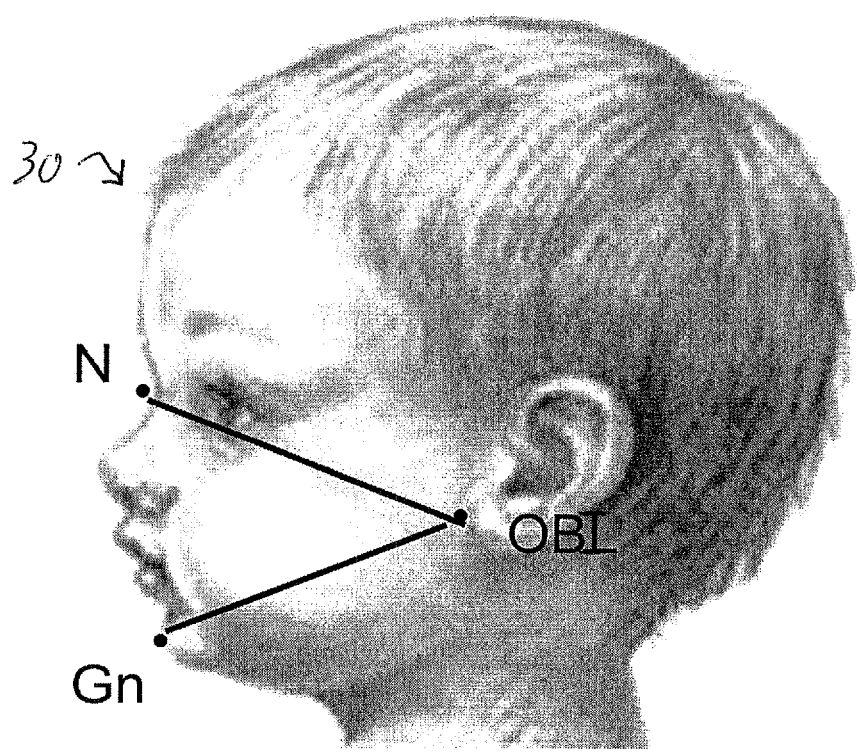
FIG. 3 is a side view of an infant with certain identified anthropometric points.

When the data are based on images (photographs) of the child, the system and method can provide the means for an un-trained person (a user) such as a parent to facilitate the measurements or estimates that are used. One manner in which this can be accomplished is to instruct the user to place markers at key facial locations on a digital facial image or images. In one non-limiting example the user can be instructed to place small dots or other markers on the right and left zygomatic arches (for a measure of the width of the face) and/or the right and left soft tissue chelion (for a measure of the width of the mouth) on a front view of the child, and/or place such markers on one or all of the otobasion inferius (OBI), the soft tissue gnathion (Gn) and the soft tissue nasion (N) on a side view of the child (where, for example, the OBI-N distance divided by the OBI-Gn distance may be termed the mandibular index). FIG. 2 illustrates a front view 20 and FIG. 3 illustrates a side view 30 with the markers (dots) in the correct locations, along with an abbreviation of the feature being marked. FIG. 2 includes abbreviations for landmarks that are not specifically referred to herein. Numerous anthropometric landmarks are available for use in the present App. As is known in the field, other landmarks, such as shown in FIG. 2, can be used in the subject app depending on the product which is being "sized to fit" a particular face. This allows customization not only to the facial recognition landmarks but also to the product being fitted.

In another embodiment the system can involve "point and click" to register the facial anthropometric landmarks. Further, the availability of facial recognition software will allow for automatic anthropometric data collection and subsequent bulb/shield calculations.

Figure 4:
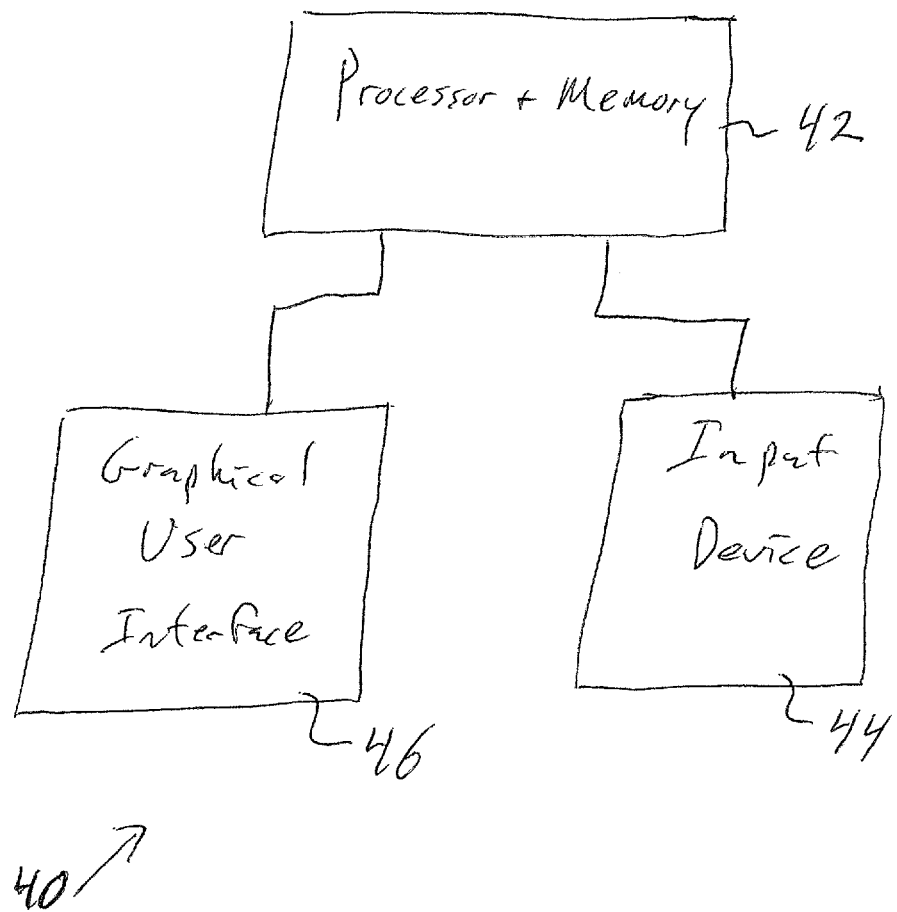
FIG. 4 is a schematic view of a system that can be used herein.

One non-limiting manner in which such markers can be placed is as follows. A software program (which can be but need not be in the form of a smartphone or other portable computing device app) directs the user to place the markers on a captured photograph or from a photo library. System 40, FIG. 4, represents the computer functionality that can be used to run the app and allow the necessary display of images of the child and any user input. Computer system 40 includes a processor and memory 42 that is functionally coupled to a graphical user interface 46 and an input device 44 (e.g., a mouse or a touchscreen that may be part of graphical user interface 46). The markers can be placed by displaying the image on the device's screen 46 and overlaying the correct number of small markers (e.g., dots as shown in FIGS. 1-3). The user is then directed to place the markers at the correct anthropometric locations on the image using input device 44. Such direction can be accomplished with written instructions, split screen animated direction and/or a short video tutorial. The software can then make the necessary distance calculations based on the dots. Other methods such as "point and click" on the anthropometric landmark (which would automatically mark the location on the image that was clicked on by the user), or automatic facial recognition of the landmarks can also be used. Distance measurements from one point to another can thereby be accomplished and the ensuing data incorporated into the calculations. Other non-distance based data (such as age, height, weight, nationality and gender) can be entered by the user. The software, through correlations, can determine measurements of other non-recorded facial and jaw features (those anthropometric points and measurements not visible in the photograph). The software can then correlate the data to the range of object(s) being fitted and display fit/sizing recommendations based on these data and the calculated measurements.

Another option is to use an off-the-shelf or specifically developed facial recognition program to determine the anthropometric data.

Pacifier sizing, by all major baby product companies, continues to be determined solely based on age of the infant (as an example: 0-3 months Stage 1; 3-6 months Stage 2; and 6-18 months Stage 3, etc.). But, as all parents know, not all three-month olds are the same weight, height or clothes size. The same is true for facial characteristics, including their face, palate, lips, nose and chin. Infant facial structure varies by age, sex, weight, genetic predisposition and ethnicity, to name a few determinative factors.

Particularly, babies have different anthropometric values for the width of their maxillary hard palate. The size of the palate increases as much in the first two years of life as it does from age 3 to 45, Pacifier use is associated with maxillary constriction and the subsequent development of unilateral and functional cross-bites. Palatal support must be provided by the use of a properly sized pacifier bulb relative to the width of the palate. Selecting the proper bulb size is important in preventing orthodontic and jaw alignment problems later.

In one specific non-limiting example pacifier bulb sizing is based on a combination of the age, the weight, the width of the mouth, the width of the face, and the width of the palate. Each of these factors may be weighted as desired, to achieve desired results. The strongest factors may be the age in months and the width of the palate. The following sets forth the considerations to determine whether to fit bulb size 1, 2, or 3, in one non-limiting example.

Age (in months): 0-3 then bulb size 1, 3-9 then bulb size 2, over 9 then bulb size 3.

Weight (in pounds): under 17 then bulb size 1, 17-25 then bulb size 2, over 35 then bulb size 3.

Width of mouth (ch-ch) (in mm): less than 28.2 then bulb size 1, 28.2-35.3 then bulb size 2, over 35.3 then bulb size 3.

Width of face (zy-zy) (in mm): less than 89.5 then bulb size 1, 9=89.5-97.3 then bulb size 2, over 97.3 then bulb size 3.

Width of palate (based on age): under age 2 months then bulb size 1, 2-6 months then bulb size 2, over 6 months then bulb size 3.

In one non-limiting example a type or size of pacifier shield is based on a combination of the weight and mandibular index; such data can be used for analysis of the lateral maxilla mandibular relationship.

As defined above OBI, Na and Gn can be used as defining soft tissue landmarks in calculating correlations with any reported mandibular index. This is important in that this type of facial analysis represents a correlation with "Apparent Life Threatening Events in Infants" including Sudden Infant Death Syndrome. When using the distance OBI-Na divide by the OBI-Gn the resulting mandibular index is predictive of jaw size and position.

The algorithm weighs the quantified mandibular index to form a recommendation on shield design, as some shields allow for free mandibular movement and are better suited for certain infants with smaller jaw types and more prone to Apparent Life Threatening Events.

Shield choice can also involve the lip length, the facial height, the ethnicity, the nose width and the age. Shield size can also be based on the bulb size, with shield size A for bulbs 1 and 2 and shield size B for bulb 3.

In the frontal view the pacifier bulb assumes a certain 'fit' in the palate. The size and design determine the contact surface of the pacifier bulb with the palate. During sucking the tongue pushes the bulb against the palate. This relationship is important in that pacifier sucking can affect the growth and development of the face and jaws in a growing child. Measurements from anthropometric data can be mathematically analyzed to predict the width of the palate and the corresponding sized pacifier bulb.

In the lateral view the pacifier shield assumes a certain 'fit' against the face. During sucking the lower jaw follows an anterior/posterior motion and the fit is in whole or in part determined by the lateral position of the lower jaw. In one example the measurements of the anthropometric data in the lateral view can direct the user to the proper shield size and design.

In one specific and non-limiting example, bulb size is determined based on the age, weight, width of mouth, width of face, and width of palate. In another specific and non-limiting example, the shield type and size is based on the mandibular index.

Common commercial pacifier bulb sizes include the following examples: NUK brand (size 3) 24 mm width; Playtex (size 3) width 20 mm; TOMMEE TIPPEE (size 3) width 24 mm; TOMMEE TIPPEE (size 2) width 20 mm.

Examples of use of variables to size a pacifier bulb according to the present disclosure include the following:

Age: 0-3 months, size 1; 3-9 months, size 2; over 9 months, size 3

Weight: under 17 pounds, size 1; 17-25 pounds, size 2; over 35 pounds, size 3

Width of mouth: less than 28.2 mm, size 1; 28.2-35.3 mm, size 2; greater than 35.3 mm, size 3

Width of face: less than 89.5 mm, size 1; 89.5-97.3 mm, size 2; greater than 97.3 mm, size 3

Examples of use of variables to type a biometric shield according to the present disclosure are set forth in this paragraph. Shield "A" is a "traditional" shield supported by the whole circumference of muscles around the oral cavity. Shield "B" is an offset shield design where the lower half of the shield is located farther from the face than is the upper half of the shield, as disclosed in the U.S. Pat. No. 9,308,152, that is incorporated herein by reference. Shield B is supported by the upper alveolus and lip during the suck and the lower jaw remains unencumbered to stay in a resting position or to open and move forward to a 'protrusive posture' (the same as during breastfeeding and nutritive sucking). Unencumbered mandibular movement encourages a clear/open airway and jaw development. Mandibular protrusion or mandibular retrusion is determined based on the mandibular index. For example, a mandibular index of 15.6 can be the measurement that is theoretical point at which it is determined whether the baby is retrognathic or prognathic. If retrognathic then the shield B is recommended. Otherwise shield A is recommended.

A number of implementations have been described. Nevertheless, it will be understood that additional modifications may be made without departing from the scope of the inventive concepts described herein, and, accordingly, other embodiments are within the scope of the following claims.

What is claimed is:

1. A method of sizing a pacifier bulb that is configured to be held or used in a child's mouth, comprising:
   providing one or more images that capture soft tissue feature of the child's face or head;
   determining, based entirely on the one or more images, the width of the child's palate; and
   sizing the bulb based at least in part on the determined width of the child's palate.

2. The method of claim 1, wherein the bulb size is determined based on the child's age, weight, width of mouth, width of face, and width of palate.

3. The method of claim 2, wherein the width of the mouth is based on the distance between two Chelion points of the child's face.

4. The method of claim 2, wherein the width of the face is based on the distance between two Zygion points of the child's face.

5. The method of claim 1, wherein the one or more images comprises a front view that includes the child's face.

6. The method of claim 1, wherein the Zygoma to Zygoma distance, the Alare to Alare distance, and the Chelion to Chelion distance are determined from the one or more images.

7. The method of claim 6, wherein the width of the palate is determined from the determined Zygoma to Zygoma distance, the Alare to Alare distance, and the Chelion to Chelion distance.

8. A method of sizing a pacifier shield for a child, comprising:
   providing one or more side view images that capture soft tissue features of the child's face or head;

determining, based entirely on the one or more images, a mandibular index of the child, wherein the mandibular index is based on an otobasion inferius to soft tissue nasion distance divided by an otobasion inferius to soft tissue gnathion distance; and sizing the shield based at least in part on the determined mandibular index.

9. The method of claim 8, further comprising fabricating the shield using the determined sizing.

10. The method of claim 9, wherein fabricating comprises 3D printing.

11. The method of claim 8, wherein the pacifier shield size is determined based on the child's mandibular index and weight.

12. The method of claim 8, wherein the pacifier shield size and shape is determined based at least in part on the child's mandibular position and mandibular size.

\* \* \* \* \*